US006994964B1

(12) United States Patent
Chang et al.

(10) Patent No.: US 6,994,964 B1
(45) Date of Patent: Feb. 7, 2006

(54) MACROMOLECULAR ARRAYS ON POLYMERIC BRUSHES AND METHODS FOR PREPARING THE SAME

(75) Inventors: Ying Chih Chang, Atherton, CA (US); Curtis W. Frank, Cupertino, CA (US); Glenn McGall, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/652,962

(22) Filed: Aug. 31, 2000

Related U.S. Application Data

(60) Provisional application No. 60/151,862, filed on Sep. 1, 1999.

(51) Int. Cl.
*C12Q 1/68* (2006.01)
*C08C 18/08* (2006.01)

(52) U.S. Cl. ............... 435/6; 435/DIG. 49; 525/50; 525/55; 525/326.1; 525/330.3

(58) Field of Classification Search ........... 435/7.1, 435/4, 6, DIG. 19, 39, 49; 436/524–531; 536/25.3; 427/264; 525/272
See application file for complete search history.

(56) References Cited

U.S. PATENT DOCUMENTS

| | | | |
|---|---|---|---|
| 4,581,429 A | 4/1986 | Solomon et al. ............. 526/220 |
| 5,143,854 A | 9/1992 | Pirrung et al. .............. 436/518 |
| 5,242,974 A | 9/1993 | Holmes .................... 525/54.11 |
| 5,288,514 A | 2/1994 | Ellman ......................... 427/2 |
| 5,312,871 A * | 5/1994 | Mardare et al. ............ 525/272 |
| 5,324,663 A | 6/1994 | Lowe ........................ 435/320.1 |
| 5,384,261 A | 1/1995 | Winkler et al. ............. 436/518 |
| 5,405,783 A | 4/1995 | Pirrung et al. ............. 436/518 |
| 5,412,087 A | 5/1995 | McGall et al. ............. 536/24.3 |
| 5,424,186 A | 6/1995 | Fodor et al. ................... 435/6 |
| 5,445,934 A | 8/1995 | Fodor et al. ................... 435/6 |
| 5,451,683 A | 9/1995 | Barrett et al. ............. 548/302.7 |
| 5,482,867 A | 1/1996 | Barrett et al. .............. 436/518 |
| 5,489,678 A | 2/1996 | Fodor et al. ............... 536/22.1 |
| 5,491,074 A | 2/1996 | Aldwin et al. ............. 435/69.7 |
| 5,510,270 A | 4/1996 | Fodor et al. ............... 436/518 |
| 5,512,131 A * | 4/1996 | Kumar et al. ............... 438/738 |
| 5,527,681 A | 6/1996 | Holmes ......................... 435/6 |
| 5,550,215 A | 8/1996 | Holmes ...................... 530/334 |
| 5,556,752 A | 9/1996 | Lockhart et al. ............... 435/6 |
| 5,571,639 A | 11/1996 | Hubbell et al. ................ 430/5 |
| 5,593,839 A | 1/1997 | Hubbell et al. ................ 435/6 |
| 5,599,695 A | 2/1997 | Pease et al. ................ 435/91.1 |
| 5,624,711 A | 4/1997 | Sundberg et al. ........... 427/261 |
| 5,631,734 A | 5/1997 | Stern et al. ................. 356/317 |
| 5,639,603 A | 6/1997 | Dower et al. ................... 435/6 |
| 5,677,195 A | 10/1997 | Winkler et al. ............ 436/518 |
| 5,677,388 A | 10/1997 | Koster et al. ............... 525/314 |
| 5,708,102 A | 1/1998 | Fryd et al. .................. 526/172 |
| 5,728,747 A | 3/1998 | Kazmaier et al. ............. 522/11 |
| 5,744,101 A | 4/1998 | Fodor et al. ................ 422/131 |
| 5,744,305 A | 4/1998 | Fodor et al. ................... 435/6 |
| 5,753,788 A | 5/1998 | Fodor et al. ............... 536/22.1 |
| 5,770,456 A | 6/1998 | Holmes ...................... 436/518 |
| 5,773,571 A | 6/1998 | Nielsen et al. ............. 530/300 |
| 5,786,461 A | 7/1998 | Buchardt et al. .......... 536/18.7 |
| 5,807,937 A | 9/1998 | Matyjaszewski et al. ... 526/135 |
| 5,831,070 A | 11/1998 | Pease et al. ............... 536/25.3 |
| 5,843,655 A | 12/1998 | McGall ......................... 435/6 |
| 5,852,129 A | 12/1998 | Kusakabe et al. ........ 525/330.3 |
| 5,856,011 A | 1/1999 | Sogabe ..................... 428/411.1 |
| 6,022,963 A | 2/2000 | McGall et al. ............. 536/25.3 |
| 6,413,587 B1 * | 7/2002 | Hawker et al. ............. 427/264 |
| 2002/0001845 A1 * | 1/2002 | Klaerner et al. ................ 436/8 |

FOREIGN PATENT DOCUMENTS

| | | |
|---|---|---|
| JP | H2-34479 | 2/1990 |
| JP | H3-99702 | 4/1991 |
| JP | 11-263819 | 9/1999 |
| JP | 2002-513668 | 5/2002 |
| WO | WO 92/20702 | 11/1992 |
| WO | WO 99/06425 | 2/1999 |
| WO | WO 99/57581 | 11/1999 |
| WO | WO 00/43539 | 7/2000 |
| WO | WO 00/61282 | 10/2000 |

OTHER PUBLICATIONS

Mrksich et al., TIBTECH Jun. 1995, vol. 13, pp. 228-235.*
Georges et al., "Narrow Molecular Weight Resins by a Free-Radical Polymerization Process," *Macromolecules*, 26: 2987-2988 (May 24, 1993).
Greszta et al., ""Living" Radical Polymerization. 1. Possibilities and Limitations," *Macromolecules*, 27:638-644 (Jan. 31, 1994).
Hawker, "Molecular Weight Control by a 'Living' Free-Radical Polymerization Process," *J. Am. Chem. Soc.*, 116: 11185-11186 (1994).
Hiltunen et al., "Effect of Catalyst and Polymerization Conditions on the Preparation of Low Molecular Weight Lactic Acid Polymers," *Macromolecules*, 30:373-379 (Feb. 10, 1997).

(Continued)

*Primary Examiner*—Andrew Wang
*Assistant Examiner*—Mark L. Shibuya
(74) *Attorney, Agent, or Firm*—Banner & Witcoff, Ltd.

(57) ABSTRACT

Polymeric brush substrates and methods for their preparation are provided. Methods are also provided for preparing macromolecular arrays on such polymeric brush substrates. Using polymeric brush substrates allows control over functional site density as well as wettability and porosity of the substrate. These polymeric brushes are useful in solid-phase synthesis of arrays of peptides, polynucleotides or small organic molecules.

6 Claims, 8 Drawing Sheets

OTHER PUBLICATIONS

Huang and Wirth, "Surface-Initiated Radical Polymerization on Porous Silica," *Analytical Chemistry*, 69:4577-4580 (Nov. 15, 1997).

Husseman et al., "Controlled Synthesis of Polymer Brushes by "Living" Free Radical Polymerization Techniques," *Macromolecules*, 32:1424-1431 (Mar. 9, 1999).

Kobayashi et al., "Silane Coupling Agent Having Dithiocarbamate Group for Photographfting of Sodium Styrene Sulfonate on Glass Surface," *J. Appl. Poly. Sci.*, 49:447-423 (Jul. 15, 1993).

Lee et al., "Polymerization of Vinyl Monomers Initiated by Chromium$^{(II)}$ Acetate+Organic Peroxides," *J. Chem. Soc. Trans. Faraday Soc. I*, 74:1726 (1978).

McGall et al., "The Efficiency of Light-Directed Synthesis of DNA Arrays on Glass Substrates," *J. Am. Chem. Soc.*, 119:5081-5090 (Jun. 4, 1997).

Prucker and Rühe, "Synthesis of Poly(styrene) Monolayers Attached to High Surface Area Silica Gels through Self-Assembled Monolayers of Azo Initiators," *Macromolecules*, 31:592-601 (1998).

Prucker and Ruehe, "Grafting of polymers to microparticulate silica by using immobilized azo initiators," *Macromolecular Chemistry II*, University Bayreuth, *Trans. Mater. Res. Soc. Jpn.* 15A:529-532 (1994).

Tovar et al., "Patterning molecularly thin films of polymers—new methods for photolithographic structuring of surfaces," *Supramol. Sci.*, 2(2):89-98 (1995).

Yamamoto et al., "Preparation of well-defined polymer brushes on silicon substrate by the surface-initiated ATRP technique and their characterization," *Polym. Prepr. (Am. chem. Sc., Div. Polym. Chem.)* 40(2):401-402 (1999).

Young and Davis, "Efficient Isolation of Genes by Using Antibody Probes," *Proc. Natl. Acad. Sci. U.S.A.*, 80:1194-1198 (Mar. 1983).

Biesalski and Rühe, "Preparation and Characterization of a Polyelectrolyte Monolayer Covalently Attached to a Planar Solid Surface," *Macromolecules*, 32:2309-2316 (Apr. 6, 1999).

Chang and Frank, "Grafting of Poly(γ-benzyl-L-glutamate) on Chemically Modified Silicon Oxide Surfaces," *Langmuir*, 12:5824-5829 (Nov. 12, 1996).

Chang and Frank, "Vapor Deposition-Polymerization of α-Amino Acid N-Carboxy Anhydride on the Silicon(100) Native Oxide Surface," *Langmuir*, 14:326-334 (Jan. 20, 1998).

English abstract of JP 11-263819.
English abstract of JP 2002-513668.
English abstract of JP H2-34479.
English abstract of JP H3-99702.

* cited by examiner

MACROMOLECULAR ARRAYS ON POLYMERIC BRUSHES AND METHODS FOR PREPARING THE SAME

CROSS REFERENCE TO RELATED APPLICATIONS

This application claims the priority benefit of U.S. Provisional Patent Application Ser. No. 60/151,862, filed Sep. 1, 1999, the contents of which are incorporated herein by reference in their entirety.

FIELD OF THE INVENTION

The present invention relates to macromolecular arrays prepared on polymeric brush substrates and methods for preparing such arrays. The invention transcends several scientific disciplines such as polymer chemistry, biochemistry, molecular biology, medicine and medical diagnostics.

BACKGROUND ART

Synthesis of high density macromolecular arrays is known. Such high density macromolecular arrays include nucleic acid arrays, peptide arrays, and carbohydrate arrays. See, for example, the U.S. Pat. Nos. 5,143,854, 5,384,261, 5,405,783, and 5,424,186.

One method of preparing macromolecular arrays involves photolithographic techniques using photocleavable protecting groups. Briefly, the method includes attaching photoremovable groups to the surface of a substrate, exposing selected regions of the substrate to light to activate those regions, attaching a monomer with a photoremovable group to the activated regions, and repeating the steps of activation and attachment until macromolecules of the desired length and sequence are synthesized. See U.S. Pat. Nos. 5,324,663, 5,384,261, 5,405,783, and 5,412,087.

Additional methods and techniques applicable to array synthesis have been described in the U.S. Pat. Nos. 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011.

Traditional substrates used in array synthesis consist of flat two-dimensional surfaces or three-dimensional surfaces such as a porous matrix or a cross-linked polymer gel. While these substrates have been satisfactory in general, as the density of the array increased, signal to noise ratio under assay conditions decreased due to crowding, resulting often in decreased performance. This crowding and performance issues become more important as more applications for high density macromolecular arrays are being developed. Thus, there is a need for high density macromolecular arrays with good or improved performance under assay conditions. The present invention meets this need.

SUMMARY OF THE INVENTION

In one embodiment, a method of preparing a polymeric brush substrate for use in solid-phase synthesis of macromolecules is provided, which method comprises:
(a) providing a substrate to which one or more free radical initiators are covalently attached, wherein each free radical initiator has a radical generation site distal to the substrate; and
(b) contacting the covalently attached substrate with monomers under conditions that promote free radical polymerization from the radical generation sites of the initiators to form a polymeric brush.

The polymerization in the above method may be accomplished by using free radical polymerization. The substrate in the above method comprises, in some aspects, glass or silica. The monomers in one embodiment comprise a vinyl group. In one embodiment, the monomers may be include for example at least two different monomers. An exemplary monomer is vinyl acetate.

The monomers in one embodiment may have the following structure:

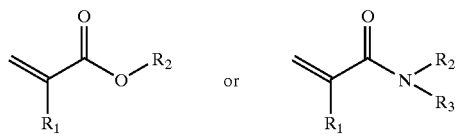

wherein $R_1$ is hydrogen or lower alkyl; and $R_2$ and $R_3$ are independently hydrogen, or —Y-Z, wherein Y is lower alkyl, and Z is hydroxyl, amino, or C(O)—R, where R is hydrogen, lower alkoxy or aryloxy.

In another embodiment, $R_2$ and $R_3$ are independently hydrogen, alkyl, alkoxy, hydroxyalkyl, polyalkylene oxide, or —Y-Z, wherein Y is linear or branched lower alkyl, aryl, alkylaryl, or polyalkylene oxide, and Z is hydrogen, hydroxyl, alkoxy, carboxy, amino, hydrazino, sulfydryl, or C(O)—R, where R is hydrogen, hydroxy, lower alkoxy or aryloxy.

The polymer formed on the support may have, for example, hydroxyl, amino, or carboxyl groups or any combination thereof.

A polymeric brush substrate capable of supporting macromolecular array synthesis comprising covalently linked monomers having for example hydroxyl, amino, sulfydryl or carboxyl groups or any combination thereof may be formed.

Methods are also provided for using the polymeric brush substrates of the above method. Methods are also provided for performing assays of macromolecular arrays prepared on the polymeric brush substrates. Such assays include hybridization assays of polynucleotides and ligand-binding assays of peptides.

The invention also provides polymeric brush substrates and polymeric brush substrates comprising macromolecular arrays prepared as disclosed herein.

A method for affixing functional sites to a surface of a solid substrate is provided, comprising:
(a) providing a substrate to which one or more free radical initiators are covalently attached, wherein each free radical initiator has a radical generation site distal to the substrate; and
(b) contacting the substrate with a mixture of linking monomers and diluent monomers under conditions that promote free radical polymerization from the radical generation sites of the initiators, wherein the density of the functional sites is determined by the ratio of functional monomers to diluent monomers.

In one aspect, the initiator is an azo type initiator. The functional site is for example amino, hydroxyl, or carboxyl. The ratio of linking monomers to diluent monomers is for example from about 1:2 to about 1:200; or in some aspects is from about 1:2 to about 1:2000 or more.

The monomers of the method have, for example, independently the following structure:

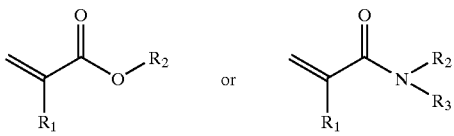

wherein $R_1$ is hydrogen or lower alkyl; and
$R_2$ and $R_3$ are independently hydrogen, or —Y-Z, wherein Y is lower alkyl, and Z is hydroxyl, amino, or C(O)—R, where R is hydrogen, lower alkoxy or aryloxy.

In another embodiment, $R_2$ and $R_3$ are independently hydrogen, alkyl, alkoxy, hydroxyalkyl, polyalkylene oxide, or —Y-Z, wherein Y is linear or branched lower alkyl, aryl, alkylaryl, or polyalkylene oxide, and Z is hydrogen, hydroxyl, alkoxy, carboxy, amino, hydrazino, sulfydryl, or C(O)—R, where R is hydrogen, hydroxy, lower alkoxy or aryloxy.

In one aspect, the monomer does not contain a free hydroxyl group and is a diluent monomer. In some aspects, the diluent monomer functions as a polymerization terminator.

In one aspect, a substrate is provided using the methods disclosed herein, wherein the density of the polymer brushes is 0.1 to 1000 pmoles of individual polymer chains per $cm^2$ of substrate surface area.

BRIEF DESCRIPTION OF THE DRAWINGS

FIG. 1A illustrates a heat generated surface radical (I) initiating polymerization of vinyl monomers (M), resulting in a tethered polymer chain on surface. FIG. 1B shows free radical polymerization on a surface, wherein initiators are covalently attached to a surface and activated by heat or light in the presence of monomers. FIG. 1C shows schematically a three-dimensional distribution of hydroxyl groups on a polymer brush substrate.

MODES OF CARRYING OUT THE INVENTION

A. General Techniques

Figure 1A:
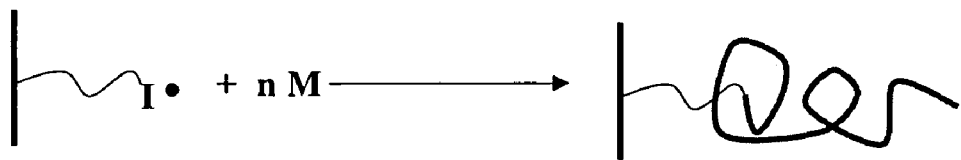
FIGS. 1A, 1B and 1C show the schematic of a polymer brush formation through free radical methods.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series* (Vols. I–IV), *Using Antibodies. A Laboratory Manual, Cells: A Laboratory Manual, PCR Primer: A Laboratory Manual, and Molecular Cloning. A Laboratory Manual* (all from Cold Spring Harbor Laboratory Press), all of which are herein incorporated in their entirety by reference.

B. Definitions

As used herein, certain terms may have the following defined meanings.

As used in the specification and claims, the singular forms "a", "an" and "the" include plural references unless the context clearly dictates otherwise. For example, the term "an array" may include a plurality of arrays unless the context clearly dictates otherwise.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

The term "molecule" generally refers to a macromolecule or polymer as described herein. However, arrays comprising single molecules, as opposed to macromolecules or polymers, are also within the scope of this invention.

"Predefined region" refers to a localized area on a solid support which is, was, or is intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct molecule is synthesized is smaller than about 1 $cm^2$ or less than 1 $mm^2$, and still more preferably less than 0.5 $\mu m^2$. In most preferred embodiments the regions have an area less than about 10,000 $\mu m^2$ or, more preferably, less than 100 $\mu m^2$. Additionally, multiple copies of the polymer will typically be synthesized within any preselected region. The number of copies can be in the thousands to the millions.

In some aspects, a predefined region can be achieved by physically separating the regions (i.e., beads, resins, gels, etc.) into wells, trays, etc.

"Solid support", "support", and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

A "protective group" is a moiety which is bound to a molecule and which may be spatially removed upon selective exposure to an activator. Several examples of protective groups are known in the literature. Activators include electromagnetic radiation, ion beams, electric fields, magnetic fields, electron beams, x-ray, and the like.

"Activating group" refers to those groups which, when attached to a particular functional group or reactive site, render that site more reactive toward covalent bond formation with a second functional group or reactive site. For example, activating groups which can be used in the place of a hydroxyl group include —O(CO)Cl; —OCH$_2$Cl; —O(CO)OAr, where Ar is an aromatic group, preferably, a p-nitrophenyl group; —O(CO)(ONHS); and the like. Activating groups which are useful for a carboxylic group include simple ester groups and anhydrides. The ester groups include alkyl, aryl and alkenyl esters and in particular such groups as 4-nitrophenyl, N-hydroxylsuccinimide and pentafluorophenol. Other activating groups are known to those of skill in the art.

A "channel block" is a material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

The terms "photolabile" and "photocleavable" are used interchangeably throughout this application.

The term "optionally substituted" refers to the presence or lack thereof of a substituent on the group being defined.

A "polymeric brush" ordinarily refers to polymer films comprising chains of polymers that are attached to the surface of a substrate. The polymeric brushes of this invention are functionalized polymer films which comprise functional groups such as hydroxyl, amino, carboxyl, thiol, amide, cyanate, thiocyanate, isocyanate and isothio cyanate groups, or a combination thereof, on the polymer chains at one or more locations. The polymeric brushes of this invention are capable of attachment or stepwise synthesis of macromolecules thereon.

A "free radical initiator" or "initiator" is a compound that can provide a free radical under certain conditions such as heat, light, or other electromagnetic radiation, which free radical can be transferred from one monomer to another and thus propagate a chain of reactions through which a polymer may be formed. Several free radical initiators are known in the art, such as azo type or nitroxide type, or those comprising multi-component systems. One example of a multi-component system is an alkyl or aryl metal and a binding ligand and a stable oxy free radical. See U.S. Pat. No. 5,312,871.

"Living free radical polymerization" is defined as a living polymerization process wherein chain initiation and chain propagation occur without significant chain termination reactions. Each initiator molecule produces a growing monomer chain which continuously propagates until all the available monomer has been reacted. Living free radical polymerization differs from conventional free radical polymerization where chain initiation, chain propagation and chain termination reactions occur simultaneously and polymerization continues until the initiator is consumed. See U.S. Pat. No. 5,677,388. Living free radical polymerization facilitates control of molecular weight and molecular weight distribution. Living free radical polymerization techniques, for example, involve reversible end capping of growing chains during polymerization. One example is atom transfer radical polymerization (ATRP).

Figure 2:
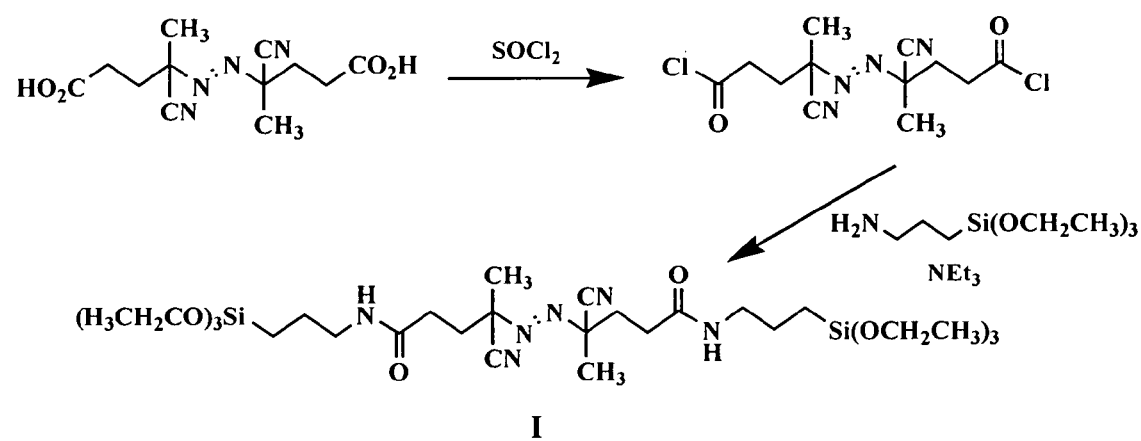
FIG. 2 show the structures and synthetic schemes for the synthesis of silane coupling agent I.

A "radical generation site" is a site on an initiator wherein free radicals are produced in response to heat or electromagnetic radiation. For example, in the case of an azo-type initiator, as shown in FIG. 2, a radical generation site exists on the carbon atom on each side of the —N=N— moiety.

A "polymerization terminator" is a compound that prevents a polymer chain from further polymerization. These compounds may also be known as "terminators," or "capping agents" or "inhibitors." Various polymerization terminators are known in the art. In one aspect, a monomer that has no free hydroxyl groups may act as a polymerization terminator.

The term "capable of supporting macromolecular array synthesis" refers to a polymeric brush that is functionalized with functional groups such as hydroxyl, amino, carboxyl etc. These functional groups permit macromolecular synthesis by acting as "attachment points." For the purposes of the present invention, those polymeric brushes that comprise functional groups only at the terminal points are not capable of supporting macromolecular array synthesis.

The term "conditions that promote free radical polymerization" refers to those conditions, including the presence of heat or electromagnetic radiation, or solvents, cosolvents, etc which allow free radical formation and propagation. Such conditions are well-known in the art, and are further described below.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers.

The monomers in a given polymer or macromolecule can be identical to or different from each other. A monomer can be a small or a large molecule, regardless of molecular weight. Furthermore, each of the monomers may be protected members which are modified after synthesis. The particular ordering of monomers within a macromolecule may be referred to herein as the "sequence" of the macromolecule.

"Monomer" as used herein refers to those monomers that are used to form polymers of the polymeric brush as well as those monomers that are used to form macromolecules on the polymeric brush. However, the meaning of the monomer will be clear from the context in which it is used. The monomers for forming the polymers of the polymeric brush have for example the general structure:

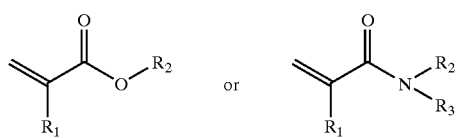

wherein R$_1$ is hydrogen or lower alkyl; R$_2$ and R$_3$ are independently hydrogen, or—Y-Z, wherein Y is lower alkyl, and Z is hydroxyl, amino, or C(O)—R, where R is hydrogen, lower alkoxy or aryloxy.

The term "alkyl" refers to those groups such as methyl, ethyl, propyl, butyl etc, which may be linear, branched or cyclic.

The term "alkoxy" refers to groups such as methoxy, ethoxy, propoxy, butoxy, etc., which may be linear, branched or cyclic.

The term "lower" as used in the context of lower alkyl or lower alkoxy refers to groups having one to six carbons.

The term "aryl" refers to an aromatic hydrocarbon ring to which is attached an alkyl group. The term "aryloxy" refers to an aromatic hydrocarbon ring to which is attached an alkoxy group. One of ordinary skill in the art would readily understand these terms.

In one aspect, the monomer is a "diluent" monomer when it does not contain a free hydroxyl group.

The monomers for preparing macromolecules of the present invention are well-known in the art. For example, when the macromolecule is a peptide, the monomers include, but are not restricted to, for example, the L-amino acids, the D-amino acids, the synthetic and/or natural amino acids. When the macromolecule is a nucleic acid, or polynucleotide, the monomers include any nucleotide. When the macromolecule is a polysaccharide, the monomers can be any pentose, hexose, heptose, or their derivatives.

As used herein, a "polynucleotide" is a sequence of two or more nucleotides. Polynucleotides of the present invention include sequences of deoxyribopolynucleotide (DNA) or ribopolynucleotide (RNA) which may be isolated from natural sources, recombinantly produced, or artificially synthesized. A further example of a polynucleotide of the present invention may be polyamide polynucleotide (PNA). The polynucleotides and nucleic acids may exist as single-stranded or double-stranded.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. 2'-O-MeORNA phosphoramidite monomers are available commercially, e.g., from Chem Genes Corp. or Glen Research, Inc. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphorothioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available from, e.g., Biosearch, Inc. (Bedford, Mass.). See also U.S. Pat. Nos. 5,773,571 and 5,786,461.

Nucleotides with modified bases can also be used in this invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability: Universal base analogues such as 3-nitropyrrole and 5-nitroindole can also be included. A variety of modified polynucleotides suitable for use in this invention are described in, e.g., "Antisense Research and Application", S. T. Crooke and B. LeBleu (eds.) (CRC Press, 1993) and "Carbohydrate Modifications in Antisense Research" in ACS Symp. Ser. #580, Y. S. Sanghvi and P. D. Cook (eds.) ACS, Washington, D.C. 1994.

When the macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by this invention. These amino acids are well-known in the art. See for example, Stryer, Biochemistry, latest edition, Chapter on amino acids and or proteins, which is incorporated herein by reference.

Methods of cyclization and polymer reversal of polymers are disclosed in copending application U.S. Ser. No. 08/351,058 which is a CIP of U.S. Ser. No. 07/978,940 which is a CIP of U.S. Pat. No. 5,242,974, incorporated herein by reference.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Methods for conducting polynucleotide hybridization assays have been well developed in the art. Hybridization assay procedures and conditions will vary depending on the application and are selected in accordance with the general binding methods known including those referred to in: Maniatis et al., "Molecular Cloning: A Laboratory Manual" 2nd Ed., Cold Spring Harbor, N.Y., 1989; Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci.*, U.S.A., 80:1194 (1983), each of which are incorporated herein by reference.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art. See, for example, Sambrook, et al., "Molecular Cloning: A Laboratory Manual," Second Edition, Cold Spring Harbor Laboratory Press, 1989; Ausubel, et al., "Current Protocols In Molecular Biology," John Wiley & Sons, 1987, 1988, 1989, 1990, 1991, 1992, 1993, 1994, 1995, 1996 and periodic updates; and Hames et al., "Nucleic Acid Hybridization: A Practical Approach," IRL Press, Ltd., 1985.

In general, conditions that increase stringency (i.e., select for the formation of more closely-matched duplexes) include higher temperature, lower ionic strength and presence or absence of solvents; lower stringency is favored by lower temperature, higher ionic strength, and lower or higher concentrations of solvents (for example, lower concentrations of formamide or dimethyl sulfoxide). The duration of the hybridization reaction and the concentration of reactants (i.e., single stranded polynucleotide) can also affect stringency, with short reaction times and low reactant concentrations favoring higher stringency.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

C. Macromolecular Arrays on Polymeric Brushes

I. Polymeric Brushes a) General Background

Polymeric brushes are known in the art. See for example, Prucker and Ruhe, *Macromolecules,* 31:592–601 (1998); Huang and Wirth, *Analytical Chemistry,* 69:4577–4580 (1997); and Husseman et al., *Macromolecules,* 32:1424–1431 (1999).

One traditional method of preparing polymeric brushes is known as "grafting." This method is typically used to prepare block copolymers wherein involves adsorbing one block of the polymer is strongly absorbed to the surface while the other block forms the brush layer. Some of the drawbacks of this adsorption-based grafting include desorption of the brush and the limited choice of functional groups for the block copolymer structure. Another method of grafting involves forming a covalent linkage between polymer chains and the substrate. Covalent linkage can be achieved by condensing a functionalized polymer with reactive surface groups on the substrate. In one such methodology, an initiator, such as a monochlorosilyl functionalized azo initiator, can be covalently attached to the substrate surface. Chain growth can be accomplished under ionic or traditional free radical polymerization conditions. These methods are shown to produce covalently attached polymer brushes with high graft densities and molecular weights. See Husseman, supra.

However, one major problem affecting the polymerization art is the inability to maintain narrow polydispersity (i.e., molecular weight distribution) at relatively high molecular weights. Moreover, obtaining the desired polymeric structure with the desired functional groups on the polymer has been a challenge. In response, "living polymerization" methods have been developed.

The term "living polymerization" refers to a polymerization process where the growing polymer chains contain one or more active sites that are capable of promoting further polymerization. See U.S. Pat. No. 5,708,102. One general strategy for obtaining living polymerization is to have a chemical species reversibly cap the active center that promotes polymerization. In ionic polymerizations initiated by anions (anionic polymerization) or cations (cationic polymerization) the counter cation or anion respectively functions as a capping agent. When the ions are bound together, polymerization stops, but reversible dissociation into ionic fragments provides a controlled source of sites that promote further ionic polymerization. Living ionic polymerizations are widely utilized in forming block copolymers by sequential addition of different alkene monomers.

Figure 1B:
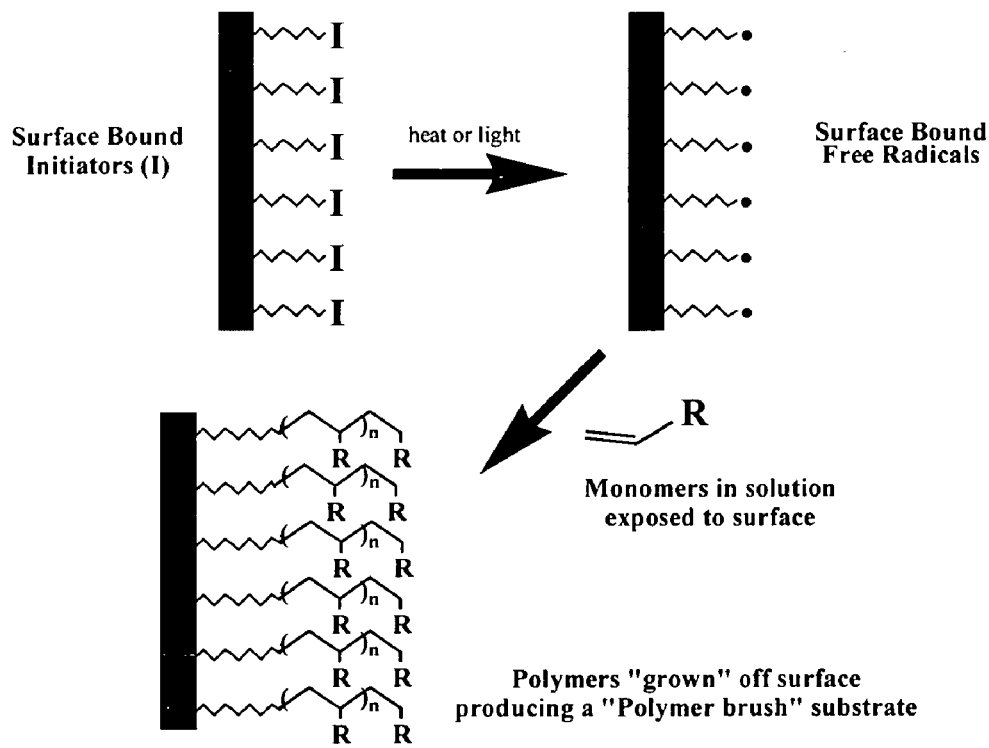
Figure 1C:
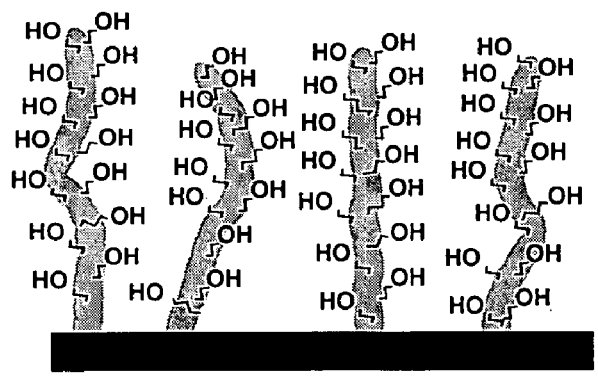

In contrast to living ionic polymerizations, living free radical polymerizations utilize polymerization initiators (R—X) that can fragment into an alkyl radical (R.) that promotes polymerization of monomers. This process can be illustrated as shown in FIGS. 1A–C. Heat or electromagnetic radiation can be used to produce the radical which initiates the polymerization of monomers. When heat is used, the initial radical can be generated spontaneously at temperatures above 100° C. or can be generated at temperatures under 100° C. by the addition of a small amount of free radical initiator. See, for example, Hawker, *Macromolecules,* 30:373–82 (1997).

At a desired stage, the polymerization is terminated by a polymerization terminator. Such terminators are known in the art. See Greszta et al., *Macromolecules,* 27:638 (1994). One approach to terminate polymerization is to react the growing radicals reversibly with scavenging radicals to form covalent species. Another approach involves reacting the growing radicals reversibly with covalent species to produce persistent radicals. Yet another approach involves allowing the growing radicals to participate in a degenerative transfer reaction which regenerates the same type of radicals. See U.S. Pat. No. 4,581,429; Hawker, *J. Am. Chem. Soc.,* 116:11185 (1994); and Georges et al., *Macromolecules,* 26:2987 (1993).

Living free radical methods allow the use of block copolymers in forming the brushes, and allow better control of polymeric structural characteristics such as molecular weight, polymeric density, branching, etc. Further, living free radical polymerization methods allow the chain elongation in the presence of different monomers such that the polymer chain can be varied.

Various types of initiators, methods of free radical generation, monomers, and free radical capping agents have been described in the prior art. See, for example, U.S. Pat. Nos. 5,677,388, 5,728,747, 5,708,102, 5,807,937, and 5,852,129. A benzoyl peroxide-chromium initiator may also be used. See Lee et al., *J. Chem. Soc. Trans. Faraday Soc. I*, 74: 1726 (1978). Additional types of initiators include α-haloester, alkoxyamine, and halobenzyl type initiators, all of which may be used in the present invention. See Husseman, supra and Hawker, supra.

Examples of photoinitiators selected in various effective amounts, such as from about 1 to about 10 weight percent based on the total weight percent of reactants, include benzoins, disulfides, aralkyl ketones, oximinoketones, peroxyketones, acyl phosphine oxides, diamino ketones, such as Micher's ketones, 3-keto courmarins, and the like, and preferably 1-hydroxycyclohexyl phenyl ketone.

Monomers include N-carboxy anhydride (for preparing peptides), styrene, and vinyl compounds. Examples of initiators include: azo-type, nitroxide type etc. An example of a terminator is a stable free radical agent known as TEMPO (2,2,6,6-tetramethyl-1-piperidinyloxy). See U.S. Pat. No. 5,728,747.

More recently, methods for producing a (meth)acrylic polymer which is hydroxyl-terminated at both ends have been reported. See U.S. Pat. No. 5,852,129. The method involves preparation of a (meth)acrylic polymer by polymerizing a (meth)acrylic monomer using an organic halide or a halogenated sulfonyl compound as an initiator and, a metal complex with a central metal selected from the elements belonging to the groups 8, 9, 10 and 11 in the periodic table as a catalyst. This (meth)acrylate polymer contains a terminal structure of the general formula: $-CH_2-C(R_1)(CO_2 R_2)(X)$. This terminal halogen is converted into a hydroxyl-containing substituent by reacting with a polymerizable alkenyl group and a hydroxyl group. The '129 patent also describes a method to introduce a hydroxyl group at each end, for example, by polymerizing a (meth)acrylic monomer using a hydroxyl-containing halide as an initiator in the above-described scheme.

b) Polymeric Brushes of the Present Invention

While the general methodology of making polymeric brushes has been known, the methods for making polymeric brushes with multiple functional groups on the brushes and the use of such multifunctionalized polymeric brushes in preparing macromolecular arrays remains to be explored.

Any support for the preparation of macromolecular arrays must provide optimal spacing of initiation sites, wettability of the surface by both organic solvents and aqueous solutions, and minimize non-specific binding of ligands to the surface. The spacing of synthesis initiation sites on a solid support can affect not only the synthesis of the array but also the binding events between an immobilized macromolecule and its ligand. The synthesis can be influenced through phenomena such as free radical formation during photolytic reaction (in light-directed synthesis), solvent accessibility and surface electrostatic effects.

The wettability of the support, or substrate surface, is also likely to have a direct influence on the yield of coupling reactions and subsequent binding events. The presentation of peptides or other ligands for recognition is expected to be a function of not only the hydrophobicity/hydrophilicity of the peptide or ligand, but also the physicochemical nature of the surface to which it is attached. Thus, hydrophilic peptide sequences are expected to extend fully into the surrounding aqueous environment, thereby maximizing their availability for recognition and binding by receptors. In contrast, hydrophobic sequences in the presence of a moderately hydrophobic substrate surface can collapse onto the surface and effectively be eliminated from the pool of available ligands presented to a receptor.

In view of the above considerations, the present invention provides polymeric brushes that allow control of functional site density, wettability and porosity.

As will become clearer from the disclosure herein and in the accompanying examples, this invention provides novel polymeric brush compositions comprise individual polymer chains, wherein the individual polymer chains include multiple functional groups, such as hydroxyl groups, for example 2, 3, 4 or more. See, for example, FIGS. 1A–C, and 6. The invention also provides methods for forming such polymeric brushes on substrates such as glass or silica.

The polymeric brush support can be tailored to provide optimal properties for synthesis and for biological assays. For example, the final concentration of functional groups (amine or hydroxyl) in the polymeric brush can be controlled by varying the relative amounts of nonfunctionalized and functionalized monomers used in forming the polymer. Additionally, the porosity and solubility of the polymer films can be controlled by varying the concentrations of monomers and crosslinking agents in the composition. Thus, a high degree of crosslinking gives a rigid insoluble polymer with low pore size, whereas omitting the crosslinking agent altogether will result in soluble linear polymer chains (with functional groups) extending off the surface of the substrate from the attachment sites.

The polymeric brushes on substrates such as glass or silica are useful for synthesizing arrays of macromolecules such as polypeptides, polynucleotides and polysaccharides or other macromolecules of interest. The polymeric brushes provide a porous three-dimensional matrix functionalized with reactive groups that serve as starting points for macromolecular array synthesis. These arrays can also be used for assays involving macromolecules such as hybridization-based nucleic acid sequence analysis or ligand-peptide or ligand-enzymatic interactions.

One of the chief advantages of these brushes is that they provide a much larger number of synthesis sites per unit area of substrate than is offered by the current generation of monofunctional silane-derivatized glass surfaces, while maintaining a similar or greater spacing between sites. The extent of binding of "target" molecules to the immobilized macromolecules is substantially increased, which enhances detection, and the multiplicity of binding sites within the polymer support may provide additional kinetic enhancement.

The lateral surface density of polymer chains can be, for example, 0.1–1000 pmoles/cm$^2$ substrate surface area, or e.g., 1–100. The lateral surface density of attachment sites on the polymer chain, wherein individual polymer chains have multiple attachment sites, can be, for example, 0.1 to 1,000,000 pmoles/cm$^2$ substrate surface area, e.g., 1–1,000.

The polymer brushes can be used to form arrays of nucleic acids. Arrays of nucleic acids immobilized on a surface are described in detail, for example, in U.S. Pat. No. 5,744,305. On a substrate, nucleic acids for example with different sequences are immobilized each in a predefined area on a surface. For example, 10, 50, 60, 100, 10$^3$, 10$^4$, 10$^5$, 10$^6$, 10$^7$, or 10$^8$ different monomer sequences may be provided on the substrate. The nucleic acids of a particular sequence are provided within a predefined region of a substrate, having a surface area, for example, of about 1 cm$^2$ to 10$^{-10}$ cm$^2$. In some embodiments, the regions have areas of less than about 10$^{-1}$, 10$^{-2}$, 10$^{-3}$, 10$^4$, 10$^{-5}$, 10$^{-6}$, 10$^{-7}$, 10$^{-8}$, 10$^{-9}$, or 10$^{-10}$ cm$^2$. For example, in one embodiment, there is provided a planar, non-porous support having at least a first surface, and a plurality of different nucleic acids attached to the first surface at a density exceeding about 400 different nucleic acids/cm², wherein each of the different nucleic acids is attached to the surface of the solid support in a different predefined region, has a different determinable sequence, and is, for example, at least 4 nucleotides in length. The nucleic acids may be, for example, about 4 to 20 nucleotides in length. The number of different nucleic acids may be, for example, 1000 or more.

The polymer brushes also may be provided on porous silica substrates having a high porosity, for example, a primarily inorganic porous substrate including a support region, and a porous region in contact with the support region, wherein the porous region includes pores with a pore size of 1–500 nm, the porous region having a porosity of, e.g., 10–90%, and a porous surface thickness of 0.01–20 µm, as described in PCT/US00/09206, the disclosure of which is incorporated herein.

c) Methods for Forming Polymeric Brushes

In one aspect, a method is provided for preparing covalently-anchored polymer brushes of amine- or hydroxy-functionalized polymers on glass or silica substrates. The polymer film is "grafted" onto the substrate covalently through a surface polymerization scheme as shown in FIGS. 1A–C and 6. An initiator is provided and one end of the initiator is covalently bound to the substrate surface, while the initiator has a radical generation site, distally from the substrate, to participate in the polymerization. Under appropriate conditions that promote free radical polymerization, monomers are contacted with the substrate. The polymeric chain is propagated to the desired length and the polymerization can be terminated when desired.

Figure 4:
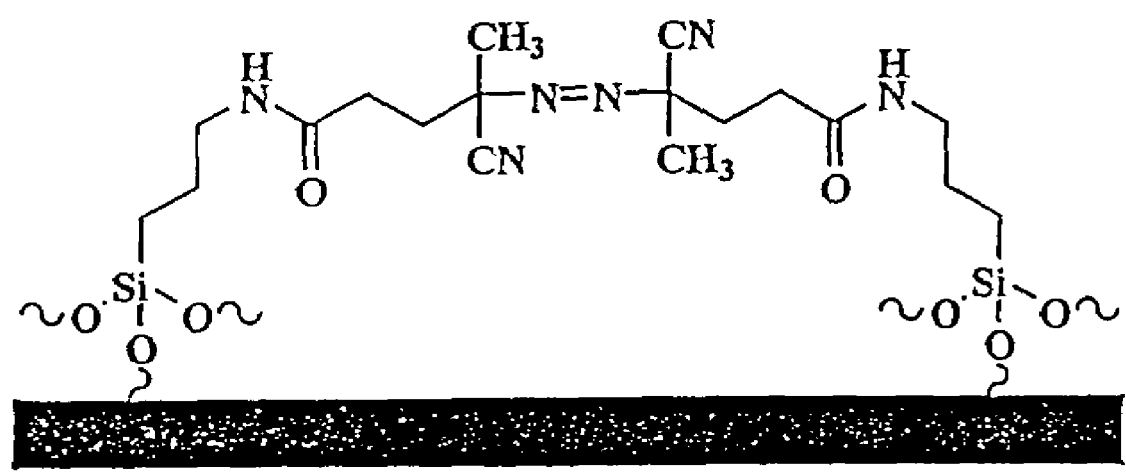
FIG. 4 shows an example of a surface-bound initiator wherein the initiator is an azo type.

In one aspect, a glass substrate is pre-silanized with an azo type initiator, such as 4, 4' azobis(pentanamide propyl triethoxysilane) (AIBN-APS) (I). See FIG. 2. The silanized substrate with the bound initiator is shown in FIG. 4. In this example, upon activation, such as by heating, $N_2$ is extruded, leaving two carbon radicals.

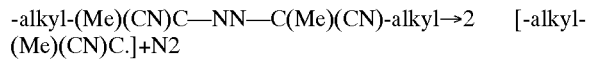

Mixtures of suitably functionalized monomers that can function as initiating points for macromolecular synthesis as well as those monomers that can function as "inert" diluents (or capping agents) are then reacted with the carbon radicals and polymerization begins. See FIG. 6. Using such a mixture of functionalized and diluent monomers, the average spacing of macromolecular synthesis initiation sites on the substrate is altered. This method provides effective control of not only functional site density but also other surface properties such as surface wettability and nonspecific binding of macromolecules.

Figure 3:
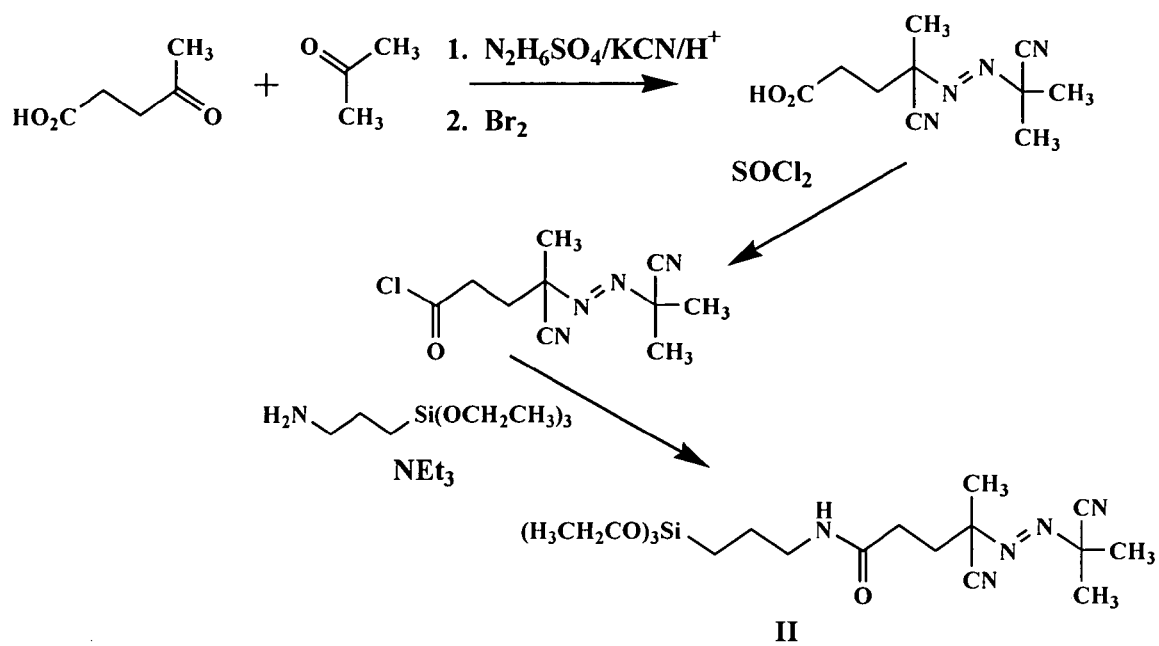
FIG. 3 shows the structures and synthetic scheme of the synthesis of silane coupling agent II.

AIBN-APS can be readily prepared by art-known methods. One exemplary method of preparation is shown in FIG. 2. Another example of an azo-type initiator (II) and its synthesis are shown in FIG. 3. See also, Chang and Frank, *Langmuir*, 12:5824–29 (1996); Chang and Frank, *Langmuir*, 14:326–334 (1998); Prucker and Ruhe, supra; Japanese Patent H1-234479; and Japanese Patent H3-99702.

Azo type initiators are described for example in Pruker and Ruhe, *Macromol.*, 31:592–601 (1998). It should be understood that the present invention is not limited to azo-type initiators. In fact, any known initiator can be used, so long as the initiator can be covalently linked to the substrate on one end while it carries a radical generation site distally to initiate polymerization.

Surface initiating sites include silane compounds, such as $(X)_a(Y)_bSi—(Z)—Q$, where b=3 minus a; X is Cl, OMe, or OEt; Y is C1–4 alkyl; Z is C2–C20 alkyl, alkylaryl or polyoxyalkylidine; and Q is a radical forming precursor group. Q is H or alkyl when a diluent silane is used.

Other initiators include nitroxyl (Husseman et al., *Macromol.*, 32:1421–31 (1999)), halo (Huang and Wirth, *Anal. Chem.*, 69:4577–80 (1997)) and thiocarbamate (Kobayashi et al., *J. Appl. Poly. Sci.*, 49:447–423 (1999)). Examples of initiator moieties include:

—C(CN)(R¹)—N=N—C(CN)(R²)R³;
—CR¹(R²)—S—C(=S)—N(R³)₂;
—CR¹(R²)—O—N(R³)R⁴; and
—C(R¹)(R²)X;

where $R^{1-4}$ are independently alkyl and X is I, Cl or Br.

The monomers are those that are capable of undergoing free radical polymerization. In one aspect, the monomer is 2-hydroxy ethyl methacrylate (HEMA), which is polymerized to provide a hydroxy functionalized vinyl polymer network. A variety of monomers that provide the desired functional groups can be used. Some monomers that meet these criteria can be represented by the generic structures shown below:

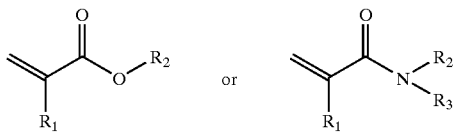

wherein $R_1$ is hydrogen or lower alkyl; $R_2$ and $R_3$ are independently hydrogen, or—Y-Z, wherein Y is lower alkyl, and Z is hydroxyl, amino, or C(O)—R, where R is hydrogen, lower alkoxy or aryloxy.

Figure 5:
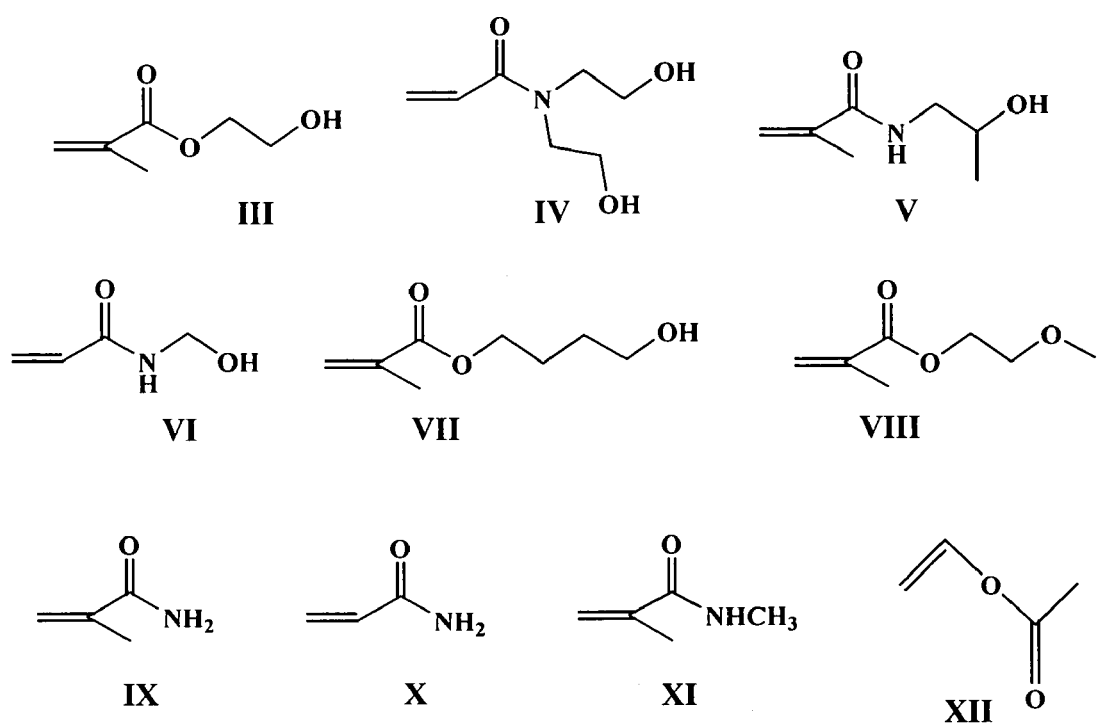
FIG. 5 shows some exemplary monomers of the present invention.
Figure 6:
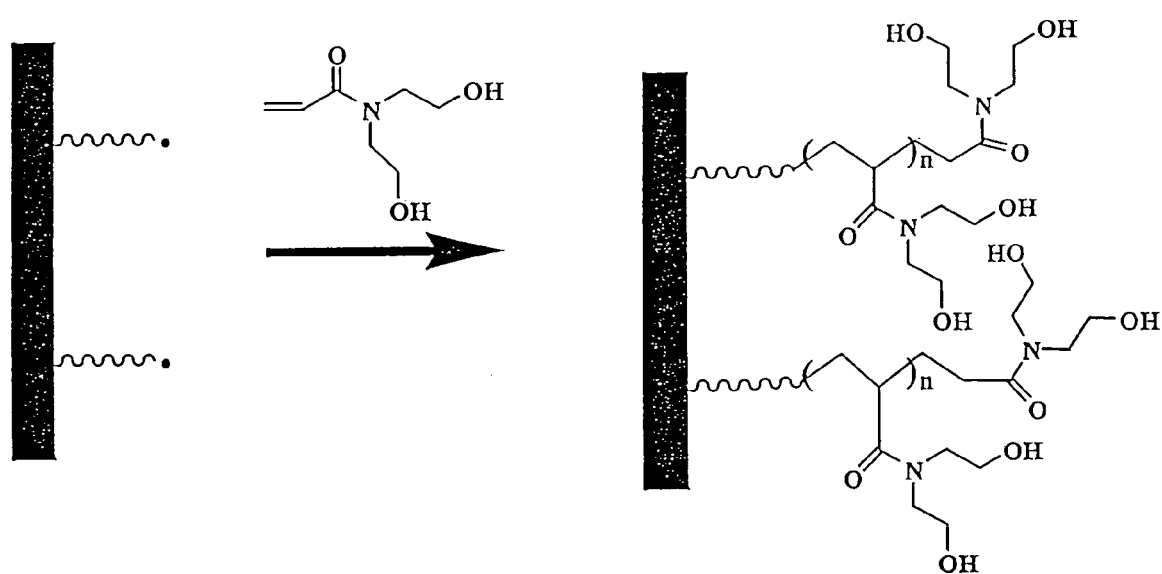
FIG. 6 shows free radical polymerization to make hydroxylated polymer brush surfaces using monomer IV.

Some specific examples of vinyl monomers that can be used in the methods of this invention are shown in FIG. 5. It is appreciated that while the specific monomers disclosed herein provide functional groups such as hydroxyl, amino, carboxyl groups, by selecting appropriately functionalized monomers, one can prepare polymeric brushes that offer additional functional groups such as thiol, cyano, isocyanate, thiocyanate or isothiocyanate. Selection of such appropriate monomers is within the ordinary skill in the art.

The resulting films exhibit excellent stability against a variety of conditions on the macromolecular arrays. Such conditions include synthesis, as well as assay conditions.

As discussed above, the polymeric brush and the silane layer can be tailored to provide optimal properties such as suitable functional group spacing, improved wettability, and minimized non-specific binding of macromolecules. For example, the thickness of the polymeric brush can be controlled by varying the polymer chain length and the number of surface initiators. The final density of functional groups (e.g. amine or hydroxyl) on the brush can be controlled simply by varying the relative amounts of non-functionalized and functionalized monomers.

In addition, the spacing between adjacent films on the brush can be controlled by interspersing polymers comprising diluent monomers. Thus, it is possible, and may be desirable in some cases, to reduce the density of polymeric films as well as the functional sites on the brush. A functional site, as used herein, refers to an attachment site on the polymer brush comprising a functional group that permits attachment of a molecule to the polymer. Surface density of initiator sites can also be varied by diluting the initiator-silane reagent with a non-functional silane such as alkyl-SiX$_3$, wherein X is a halogen or alkoxy. The porosity and solubility of the polymeric brushes can be controlled by varying the concentrations of vinyl monomers, crosslinking agents, and surface initiators in the composition.

The free radical polymerization is typically conducted for a sufficient amount of time, such that the desired conversion is achieved. The amount of time needed may depend upon the temperature of the polymerization. In some aspects, the lower the temperature, the longer the amount of time needed to achieve a desired conversion. Typically, the polymerization is conducted from about 1 to about 20 hours, preferably from about 1.5 to about 10 hours, more preferably from about 2 to about 8 hours and most preferably from about 2.5 to about 6 hours.

The polymer produced by the process of the present invention can have a variety of molecular weights. In some aspects, the molecular weight may depend on the amount of initiator used, because the amount of initiator used may determine how many chains are initiated.

The polymerization reactions may be conducted in a variety of media, for example suspension, emulsion, bulk, that is neat or without solvent, or in aqueous or nonaqueous solution. When used, suitable solvents include aromatic hydrocarbons, such as benzene, toluene, xylenes, pyridines or other solvents that have comparably small chain transfer constants with the particular monomer(s) used in the polymerization. The polymerization can be carried out at temperatures ranging from about −80° C. to about 80° C. The preferred reaction temperature range may be from about 25° C. to about 70° C. Any of the known class of polymerization initiators is suitable provided it has requisite solubility in the solvent or monomer mixture chosen and has an appropriate half-life at the temperature of polymerization. In some aspects, the initiator has a half-life that is short when compared to the total time required for the polymerization process. The process of the invention is carried out preferably as a batch process, but when needed can be carried out in any of the standard polymerization processes, for example semi-batch, starved feed, or continuous processes.

The polymerization reactions of the present invention can in some aspects be supplemented with a solvent or cosolvent to help ensure that the reaction mixture remains a homogeneous single phase throughout the monomer conversion. Any solvent or cosolvent may be selected providing that the solvent media is effective in permitting a solvent system which avoids precipitation or phase separation of the reactants or polymer products until after all polymerization reactions have been completed.

Exemplary solvents or cosolvents include polymer product compatible aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives, such as butyl CARBITOL™ or CELLOSOLVE™, amino alcohols, ketones, and the like, derivatives thereof, and mixtures thereof. When mixtures of water and water soluble or miscible organic liquids are selected as the reaction media, the water to cosolvent weight ratio typically ranges from about 100:0 to about 10:90, and preferably from about 97:3 to about 25:75.

The polymerization reaction rate of the monomers may be accelerated and the reaction time reduced by the addition of a catalytic amount of a protic acid that will not also initiate cationic polymerization. The protic acid may be selected from the group consisting of organic acids such as sulfonic, phosphoric, carboxylic acids, camphor sulfonic acid and nitroxides containing acid functional groups, such as 3-carboxyl-proxyl. Suitable amounts can be easily determined with ordinary skill.

The polymerization process of the present invention may be repeated a number of times within the same reaction vessel by the delayed and stepwise addition of more monomer or monomers with varying amounts of initiators and terminating agents.

The processes of the present invention can be selected to form a wide variety of polymers. Further, the process of the present invention can be selected to polymerize a mixture of two or more different polymerizable monomers to form copolymers therefrom.

Optionally, known additives may be selected in the polymerization reactions, which additives may provide performance enhancements to the resulting product. Such additives may include colorants, lubricants, release or transfer agents, surfactants, stabilizers, antifoams, and the like.

II. Methods of Preparing Macromolecular Arrays on Polymeric Brush Substrates a) General Examples of macromolecules that can be prepared on polymeric brush substrates of this invention include nucleic acids and polynucleotides comprising both linear and cyclic nucleotides, peptides, polysaccharides, phospholipids, heteromacromolecules in which a known drug is covalently bound to any of the above, polyurethanes, polyesters, polycarbonates, polyureas, polyamides, polyethyleneimines, polyarylene sulfides, polysiloxanes, polyimides, polyacetates, or other macromolecules which will be apparent upon review of this disclosure. Such macromolecules are "diverse" when different (i.e., non-identical) monomers are used at different predefined regions of a substrate.

It should be understood that any multifunctionalized polymeric brush substrate, can be used to prepare macromolecular arrays of this invention. Thus, the polymeric brush substrates contemplated for the purposes of preparing macromolecular arrays are not limited to the above-described polyhydroxy functionalized or polyamino acrylate polymeric brush substrates.

The above-described macro molecular arrays can be prepared on the polymeric brush substrates above using a number of art-known methods, including light-directed methods, flow channel and spotting methods, pin-based methods and bead-based methods.

b) Light-Directed Methods

"Light-directed" methods (which are one technique in a family of methods known as VLSIPS™ methods) are described in U.S. Pat. No. 5,143,854, incorporated by reference. The light directed methods discussed in the '854 patent involve activating predefined regions of a substrate or solid support and then contacting the substrate with a preselected monomer solution, comprising monomers that are protected with photolabile protecting groups. The predefined regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

Using photolithographic techniques described above, the photolabile protecting groups can be removed in one preselected area and a monomer bearing a chemically-removable protecting group is attached. Standard, chemically-removable protecting groups include those groups which are commercially available and which are known to be removable under typical chemical conditions. Examples of such protecting groups include FMOC, DMT, BOC, t-butyl esters and t-butyl ethers. See also copending U.S. Provisional Application No. 60/146,574, filed Jul. 30, 1999, and copending application Ser. No. 08/630,148, filed Apr. 10, 1996 for additional disclosure of suitable protecting groups.

Following the attachment of such a protected monomer, the protecting group is removed. Conditions for the removal are known in the art. See, for example, Greene, et al., Protective Groups In Organic Chemistry, 2nd Ed., John Wiley & Sons, New York, N.Y., 1991, incorporated herein by reference. The reactive functionality which was previously protected with the chemically-removable protecting group is then re-protected with a photolabile protecting group, using, for example, a derivative of the formula:

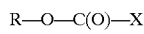

in which R is a photo-cleavable moiety (e.g., o-nitrobenzyls, pyrenylmethyl, Ddz, various benzoin groups, bromonitroindole) and X is a suitable leaving group (e.g., Cl, F, pentafluorophenoxy, p-nitrophenoxy, N-succinimidyloxy, adamantanecarboxy, or tetrazolyl).

The re-protection of surface functional groups with such reagents is typically carried out in an organic solvent containing a non-nucleophilic base (e.g., 2,6-lutidine, pyridine, triethylamine or diisopropylethylamine). In some embodiments, a nucleophilic catalyst (e.g., N-methylimidazole, hydroxybenzotriazole or 4-(N,N-dimethylamino) pyridine) is also included to provide further enhancement of the rate and efficiency of the re-protection step. Following the addition of the photolabile protecting groups, the VLSIPS™ cycles can be continued using photolithographic deprotection, followed by coupling of an additional monomer, protecting group replacement, etc., until the desired macromolecular array is completed.

In one aspect, the macromolecule produced is a polynucleotide. Standard phosphoramidite chemistry or H-phosphonate methods or other coupling methods known to those of skill in the art can be used for monomer coupling monomers. Additionally, the photolabile protecting group which is illustrated (MeNPOC) can be replaced with another photolabile protecting group such as NVOC, or those photolabile protecting groups described in co-pending applications as referred to above. Once the chemically-removable protecting group has been removed, a photolabile protecting group can be added using a mixed anhydride of the protecting group.

In another aspect, the macromolecule is a peptide. For peptide synthesis, commercially-available amino acids having chemically-removable protecting groups can be used, for example FMOC-amino acids. After exchange of the protecting groups, the coupling steps can be carried out using BOP/HOBt activation and coupling methods. Those of skill in the art will understand that other coupling methods as well as other amino acid monomers having chemically-removable protecting groups can be used in the present invention.

In still another aspect, all preselected areas are derivatized with a first monomer, each of the monomers having a chemically-removable protecting group. Following the addition of the first monomer to each of the preselected regions, the protecting groups are all removed in a single step using chemical deprotection in the form of a wash across the solid support. Alternatively, vapor-phase deprotection can also be used. See the U.S. Pat. Nos. 5,599,695, and 5,831,070. Reprotection of each of the growing macromolecule with a photolabile protecting group is then carried out in the form of another wash across the entire solid support. Following this reprotection, photolithographic techniques of macromolecule synthesis can be continued using monomers having chemically-removable protecting groups.

c) Flow Channel or Spotting Methods

Additional methods applicable to array synthesis on a single substrate are described in U.S. Pat. Nos. 5,677,195 and 5,384,261, incorporated herein by reference. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the present invention can generally be described as follows. Diverse macromolecules are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously.

d) Pin-Based Methods

Pin-based methods for the preparation of macromolecular arrays are described in detail in U.S. Pat. No. 5,288,514. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of polynucleotides, for example, the spacer may be selected from a wide variety of molecules which can be used in organic environments associated with synthesis as well as aqueous environments associated with binding studies.

Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., Solid Phase Peptide Synthesis, IRL Press (1989), incorporated herein by reference. In some aspects, the spacer may provide for a cleavable function by way of, for example, exposure to acid or base.

e) Bead Based Methods

A general approach for bead based synthesis is described in the U.S. Pat. No. 5,384,261. For the synthesis of molecules such as polynucleotides on beads, a large plurality of beads are suspended in a suitable carrier (such as water) in a container. The beads are provided with optional spacer molecules having an active site. The active site is protected by an optional protecting group.

In a first step of the synthesis, the beads are divided for coupling into a plurality of containers. For the purposes of this brief description, the number of containers will be limited to three, and the monomers denoted as A, B, C, D, E, and F. The protecting groups are then removed and a first portion of the molecule to be synthesized is added to each of the three containers (i.e., A is added to container 1, B is added to container 2 and C is added to container 3).

Thereafter, the various beads are appropriately washed of excess reagents, and remixed in one container. Again, it will be recognized that by virtue of the large number of beads utilized at the outset, there will similarly be a large number of beads randomly dispersed in the container, each having a particular first portion of the monomer to be synthesized on a surface thereof.

Thereafter, the various beads are again divided for coupling in another group of three containers. The beads in the first container are deprotected and exposed to a second monomer (D), while the beads in the second and third containers are coupled to molecule portions E and F respectively. Accordingly, molecules AD, BD, and CD will be present in the first container, while AE, BE, and CE will be present in the second container, and molecules AF, BF, and CF will be present in the third container. Each bead, however, will have only a single type of molecule on its surface. Thus, all of the possible molecules formed from the first portions A, B, C, and the second portions D, E, and F have been formed.

The beads are then recombined into one container and additional steps such as are conducted to complete the synthesis of the polymer molecules. In a preferred embodiment, the beads are tagged with an identifying tag which is unique to the particular double-stranded oligonucleotide or probe which is present on each bead. A complete description of identifier tags for use in synthetic libraries is provided in the U.S. Pat. No. 5,639,603.

Applications

The advent of methods for the synthesis of diverse molecules on solid supports has resulted in the genesis of a multitude of diagnostic applications for such arrays. A number of these diagnostic applications involve contacting a sample with a solid support, or chip, having multiple attached biological macromolecules such as peptides and polynucleotides, or other small ligand molecules synthesized from building blocks in a stepwise fashion, in order to identify any species which specifically binds to one or more of the attached polymers or small ligand molecules.

Methods for making arrays of polynucleotide probes that can be used to provide the complete sequence of a target nucleic acid and to detect the presence of a nucleic acid containing a specific polynucleotide sequence have been described. U.S. Pat. No. 5,556,752 describes methods of making arrays of unimolecular, double-stranded polynucleotides which can be used in diagnostic applications involving protein/DNA binding interactions such as those associated with the p53 protein and the genes contributing to a number of cancer conditions. Arrays of double-stranded polynucleotides can also be used to screen for new drugs having particular binding affinities. More recently, complete n-mer array probes with a wide scope of general applicability have been described. See U.S. Provisional Application No. 60/100,393, filed Sep. 15, 1998; and U.S. Ser. No. 09/394,230, filed Sep. 13, 1999.

It will be apparent to those of skill in the art that the methods and compositions of the present invention will find application in any of the above-noted processes for solid phase synthesis of arrays of biological polymers and small molecules as well as in any of the above-noted assay methods.

EXAMPLES

The following examples are offered solely for the purposes of illustration, and are intended neither to limit nor to define the invention.

Example 1

Preparation of Polymeric Brushes

Soda lime glass or silicon (100) substrates are cleaned with piranha solution (30% of hydrogen peroxide and 70% of sulfuric acid) at 90° C. for 30 minutes, washed with copious amount of deionized water and dried with a stream of $N_2$. The cleaned substrate is then silanized with azobis (pentanamide propyl triethoxysilane), known as AIBN-APS, structure and preparation of which are shown in FIG. 2. See Japanese Patent H1-234479; and Japanese Patent H3-99702. The method consists of immersing the glass or silica substrate in a 1% of AIBN-APS solution in toluene for several hours. After reaction, the substrate is washed with fresh toluene and dried with a stream of $N_2$. The reaction progress of silanation on silica can be monitored by ellipsometric thickness measurements.

The AIBN-APS -silanized substrate is subjected to radical polymerization. The substrate is immersed in a 25–50% solution of 2-hydroxy ethylmethacrylate (HEMA) in degassed DMF for various reaction times and temperatures. At a reaction temperature of 70° C., the surface AIBN molecule dissociated into two radicals, initiating polymerization to form hydroxyl-functionalized methacrylate polymer. The substrates were then washed thoroughly with DMF and water, and thoroughly dried. The resulting film thickness on silicon is monitored by ellipsometry or AFM (atomic force microscopy). For example, a range of 5–30 nm thick pHEMA film is obtained after a 24-hour polymerization.

Additional details for preparing polymeric brushes are known in the art. See for example, U.S. Pat. Nos. 5,852,129, 5,728,747, 5,807,937, 5,708,102, and 5,6.77,388. See also, Chang and Frank, *Langmuir*, 12: 5824–29 (1996); Chang and Frank, *Langmuir*, 14: 326–334 (1998); Prucker and Ruhe, supra; Japanese Patent H1-234479; and Japanese Patent H3-99702.

Example 2

Preparation of Polynucleotide Array on Polymeric Brushes

A 5 nm thick pHEMA film on a glass substrate was used. Fluorescein molecules are attached to the surface by standard procedures as described for example in PCT/US00/09206. A representative control silanated substrate, flat soda lime glass, silanated with bis (2-hydroxyethyl)-3-aminopropyltriethoxysilane, and the pHEMA modified glass were compared.

Fluoreprime Stain Assay

Quantitative studies of the synthesis, density and uniformity of silica substrates was conducted using methods based on surface fluorescence as described in McGall et al; *J. Am. Chem. Soc.*, 119: 5081–5090 (1997). Fluorescent "staining" of the surface was performed as described, with the exception that a fluorescein concentration of 0.5 mM in a solution containing 50 mM DMT-T-CEP in acetonitrile was used. The fluorescein phosphoramidite is coupled to the free hydroxyl groups with the standard protocol. Substrates are then deprotected for a minimum of one hour in a 1:1 solution of ethylenediamine/ethanol, rinsed with deionized water, and blown dry with dry nitrogen. The substrate is then scanned using confocal microscopy. The signal obtained is a function of the number of available hydroxyl groups on the surface. In this case, the relative values as compared to other types of similarly treated glass is an indication of the relative density and capacity of the surface. This technique also provides a visual picture of the surface with respect to quality and uniformity of the surface. The technique is not limited to hydroxyl groups but may be modified to measure other groups of interest for support of polymer of interest on the surface by using the appropriately functionalized molecule for detection.

Figure 7:
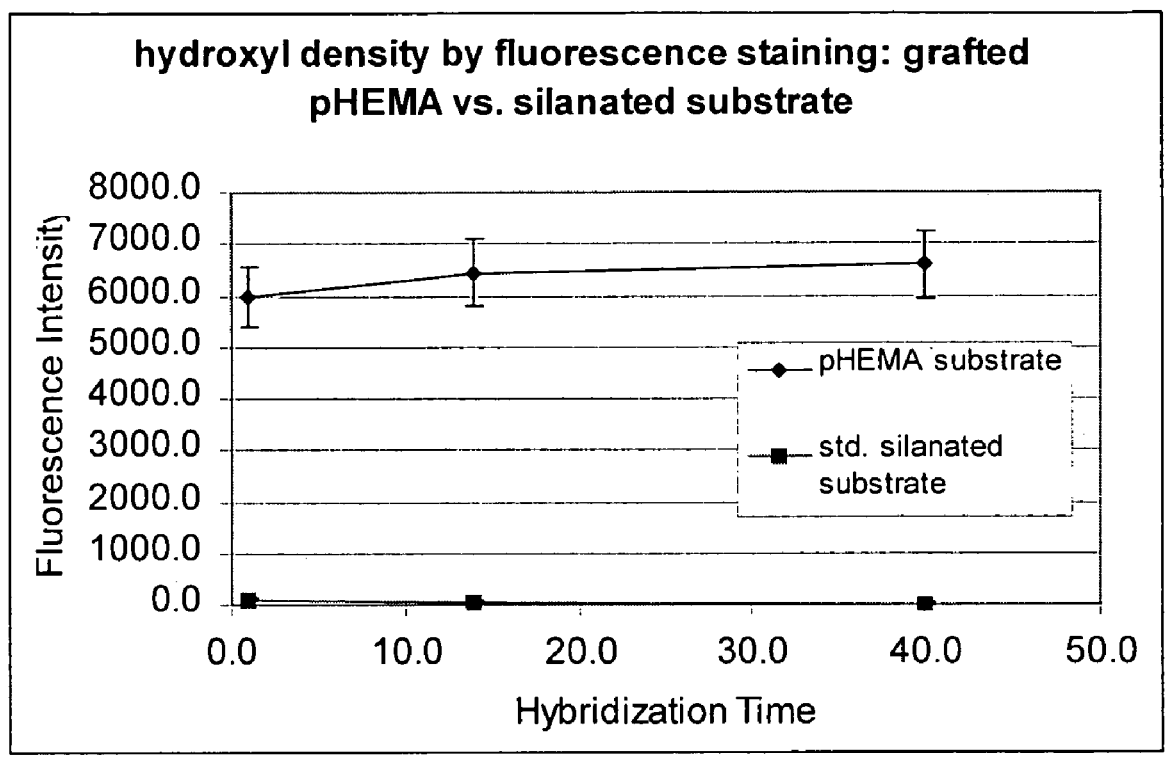
FIG. 7 shows a comparison of hydroxyl functional group densities on polymeric brushes v. flat two-dimensional substrates.

The pHEMA film had a much higher hydroxyl content/unit area of the substrate as evidenced by fluorescent staining analysis. As shown in FIG. 7, the average fluorescent intensity from the fluorescein-stained stripe on the pHEMA-modified glass was at least 60-times higher than the BIS-silane control initially, and this increases to a >300-fold higher ratio after a 40-hour period in 6× SSPE buffer at 25° C. This increase is primarily due to a loss of the fluorescence intensity on the control substrate due to the known hydrolysis of the "bis" silane bonded phase in aqueous phosphate buffers. It appears, then that the pHEMA film is more stable towards hydrolytic degradation than the silanated layer.

HPLC Quantitation Assay

The HPLC quantitaion assay is performed substantially as described in U.S. Pat. No. 5,843,655. HPLC (high performance liquid chromatography) analyses are performed on a Beckman System Gold ion exchange column using fluorescence detection at 520 nm. Elution is performed with a linear gradient of 0.4M $NaClO_4$ in 20 mM Tris pH 8, at a flow rate of 1 mL/min, or other suitable buffer system. The HPLC quantitation assay is used to measure the site density available for generating polymers, and the coupling efficiency of each subsequent addition of monomer to the growing chain.

In this technique, attached to the surface were a cleavable sulfone linker (5'-phosphate-ON reagent, ChemGenes Corporation), a spacer molecule ("C3," a three carbon spacer phosphoramidite from Glen Research), and a fluorophore (5-carboxyfluorescein-CX CED phosphoramidite from BioGenex). The purpose of the spacer molecule is to discriminate between fluorescent molecules that have attached to the intended synthesis sites vs. those that have remained on the surface without chemical attachment. Synthesis was also accomplished on the surfaces using traditional acid-based polynucleotide chemistry (trityl chemistry). Similar chemistries can be applied for the synthesis of polynucleotide, peptide, oligosaccarides, peptide nucleic acids, and other polymers. The description relating to the peptide nucleic acids can be found in the PCT publication WO92/20702, published Nov. 26, 1992.

After synthesis the surface is treated with a known solution volume of reagent necessary to cleave the linker to release 3'- $C_3$-fluorescein-5', and this is typically cleaved in solution overnight (1:1 by volume ethylenediamine/water). The resulting solution is diluted and coinjected with an internal standard onto and analyzed by HPLC. The internal standard is a 3'-$C_3$—$C_3$-fluorescein-5' chain prepared separately on an ABI synthesizer. Concentration is determined by UV-Vis spectra on a Varian Cary 3E spectrophotometer (Varian). Integration of HPLC peak areas can be used to determine total site density and cleanliness of coupling.

The control silanized substrates had a density of hydroxyl groups of 110 pmoles/cm$^2$, whereas the pHEMA modified glass had a density of hydroxyl groups of 11,800. Thus the pHEMA modified glass included 107 times more hydroxyls per unit area.

Example 3

Hybridization Assay on Polymeric Brush Arrays of Polynucleotides

The polynucleotide polymeric brush array included polynucleotides attached to a pHEMA coated glass substrate made as described in Example 1.

Full length probes capable of hybridization, typically 20-mer probes, were synthesized using Affymetrix synthesizers as described in U.S. Pat. No. 5,405,783, using nucleoside phosphoramidites equipped with 5'-photolabile MeNPOC protecting groups. The sequence used was a 20 mer probe such as (3')-AGG TCT TCT GGT CTC CTT TA (5') (SEQ ID NO:1), with the 3' end attached to the surface. The non-photolabile protecting groups were removed post synthesis in 1:1 ethylenediamine/ethanol (v/v) for a minimum of 4 hours.

Hybridization assays were performed on glass slides without further processing. Each slide was placed in about 10–15 mls of 10–50 nM target oligonucleotide in hybridization buffer with gentle stirring. The two hybridization buffers used is 6× SSPE. The target sequence is the exact complement of the probe sequence, such as: (5') Fluorophore- TCC AGA AGA CCA GAG GAA AT (SEQ ID NO:2).

The pattern and intensity of surface fluorescence was imaged with a specially constructed scanning laser confocal fluorescence microscope. Where necessary, the photon multiplier tube gain was adjusted to keep signals within range for the detector.

The polynucleotide polymeric brush array was hybridized from one hour to several hours with control oligonucleotide (10 nM in 6× SSPE) at various temperatures. Standard hybridization protocols were used, as described, for example, in PCT/US00/09206. Any equivalent hybridization protocol known in the art can also be employed.

Figure 8:
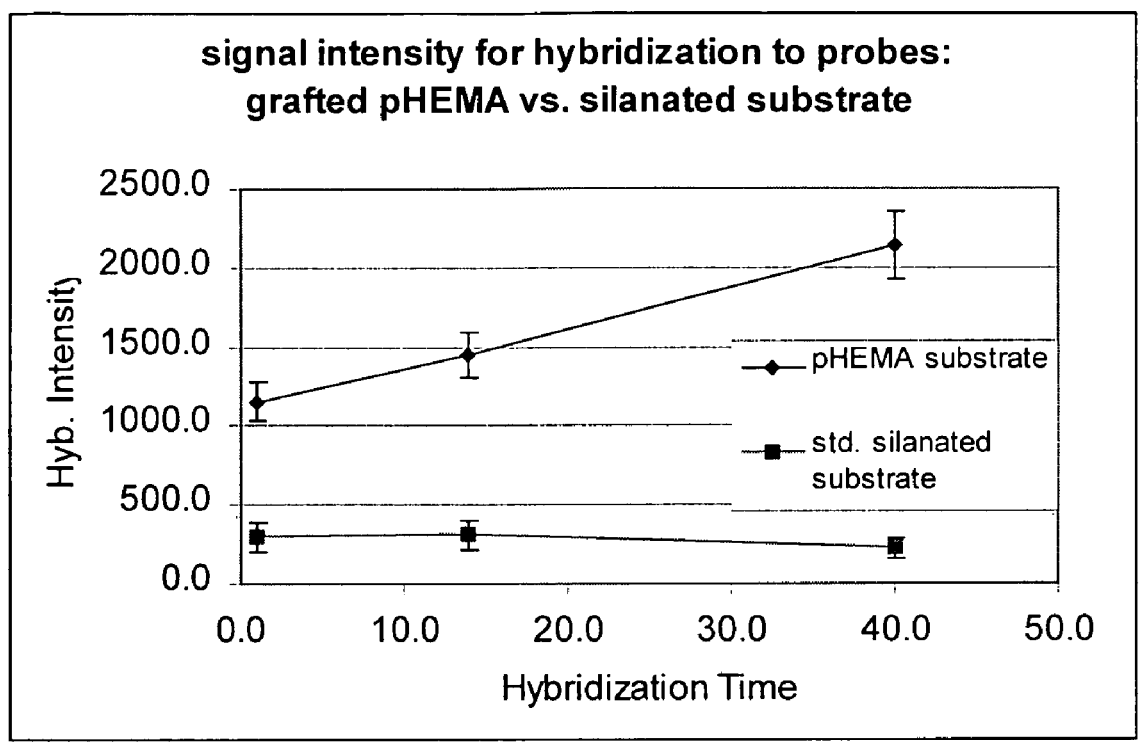
FIG. 8 shows a comparison of signal intensity from hybridization on a polymeric brushes v. flat two-dimensional substrates.

With respect to hybridization characteristics, synthesis on the pHEMA film also gives a much higher surface concentration of probes, and this results in substantially higher hybridization signals. FIG. 8 shows the hybridization signal ratio developed in 40 hours. The intensity ratio, initially ~5× higher than the control, increases to ~9 times higher after 40-hour period of hybridization. Hybridization signal continues to increase on the film with time, whereas the silanated substrate is already saturated at the 1 hour time point. Apparently, while the pHEMA film clearly has a much higher surface hydroxyl content, and capacity for binding target molecules, the kinetics of binding may be somewhat slower. This would be the expected result from crowding of the probes on the fully hydroxylated polymer "brush", leading to substantial inaccessibility of the probes.

A lower hydroxyl concentration is likely to be more optimal, as greater probe spacing improves their accessibility to target molecules in solution. Dilution of the probe concentration in the film can be achieved by carrying out the polymerization with a mixture of functional and non-functional monomers to form a copolymer with functional groups spaced further apart along the chains. Such "diluted" functionalized polymeric brush substrates are envisioned to provide optimal probe density (which is still comparable to or greater than that obtainable on traditional substrates), while providing comparable or greater signal.

After approximately 40 hours of hybridization, the temperature was raised to 45° C., which resulted in rapid decrease in signals for both the control and pHEMA modified substrates. This is due to the dissociation of the bound target molecules from the surface probes as the duplex is destabilizied with increasing temperature. However, there is no observable decrease in the signal ratio of the pHEMA sample to the control substrate, suggesting that hybridization affinities of the oligonucleotide probes are equivalent on both substrates.

In another experimental run, in a hybridization on a substrate made as in Example 1, the hybridization in SSPE (sodium chloride, sodium phosphate, EDTA) buffer was 2.3× higher than the control at 25° C. at 1 hr. After 45° C. for 16 hours, the intensity increased 135 fold higher than the standard.

All publications, patents and patent applications referred to herein are incorporated herein by reference in their entirety.

The above description is illustrative and not restrictive. Many variations of the invention will become apparent to those of skill in the art upon review of this disclosure. Merely by way of example a variety of substrates, polymers, initiators, synthesis initiation sites, and other materials may be used without departing from the scope of the invention.

The invention claimed is:

1. A method of preparing a polymeric brush substrate having a plurality of polynucleotides thereon for use in a polynucleotide array, the method comprising:
   (a) providing a substrate to which one or more free radical initiators are covalently attached, wherein each free radical initiator has a radical generation site distal to the substrate;
   (b) contacting the covalently attached substrate with monomers under conditions that promote free radical polymerization from the radical generation sites of the initiators to form a polymeric brush; and
   (c) covalently attaching a plurality of polynucleotides to a plurality of reactive groups on the polymeric brush.

2. The method of claim 1, wherein step (b) comprises living free radical polymerization.

3. The method of claim 1, wherein the substrate comprises glass or silica.

4. The method of claim 1, wherein the monomers comprise a vinyl group.

5. The method of claim 1, wherein the polymer brush formed on the support comprises hydroxyl, amino, carboxyl, or sulfydryl groups or a combination thereof.

6. The method of claim 1, wherein the monomers comprise vinyl acetate.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: hybridization probe

```
<400> SEQUENCE: 1
atttcctctg gtcttctgga                                               20

<210> SEQ ID NO 2
<211> LENGTH: 20
<212> TYPE: DNA
<213> ORGANISM: Artificial Sequence
<220> FEATURE:
<223> OTHER INFORMATION: hybridization probe
<220> FEATURE:
<221> NAME/KEY: misc_feature
<222> LOCATION: (1)..(1)
<223> OTHER INFORMATION: fluorophore

<400> SEQUENCE: 2
tccagaagac cagaggaaat                                               20
```